United States Patent [19]

Ryan

[11] Plant 4,260

[45] June 6, 1978

[54] IMPATIENS PLANT — CHICKASAW

[76] Inventor: John J. Ryan, 39877 Sundale Dr., Fremont, Calif. 94538

[21] Appl. No.: 782,286

[22] Filed: Mar. 28, 1977

[51] Int. Cl.[2] ..... A01H 5/00

[52] U.S. Cl. ..... Plt./68

[58] Field of Search ..... Plt./68

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of New Guinea Impatiens plant known by the cultivar name Chickasaw, and discovered by me in commercial greenhouses in Fremont, Calif. Chickasaw is closest in characteristics to Longwood's Painted Lady but is particularly characterized by short internodes; its floriferousness of rose-pink flowers in the summer and salmon flowers in the winter as opposed to Painted Lady whose color is not as dark; a bright yellow variegation on a moderately light green leaf under high light and increasing age of plant as opposed to Painted Lady which has no variegation; and a stem and breaking action conductive to making a good basket plant.

2 Drawing Figures

BACKGROUND OF THE INVENTION

The present new variety (seedling 76-22-1) was discovered by me in a commercial greenhouse in Fremont, Calif. as a result of the cross pollination of unpatented pistil parent 75-8 and unpatented pollen parent 75-14.

Asexual reproduction of my new cultivar by terminal or stem cuttings grown in hanging baskets in a plastic (polyethylene) greenhouse in Fremont, Calif. under normal environmental conditions show that the characteristics described come true to form and are established and transmitted through succeeding propagations.

Color readings were taken during daylight hours in full sun, and all colors are based on the Royal Horticultural Society Colour Chart.

BRIEF SUMMARY

Chickasaw is closest in characteristics to Longwood's Painted Lady. The following outstanding characteristics of Chickasaw distinguish it from Longwood's Painted Lady:

1. Flower ability equals or surpasses Painted Lady.
2. Flower color is salmon to rose-pink, depending on light intensity; Painted Lady is not as dark.
3. Variegation is a bright yellow on a moderately light green leaf; high light and age are needed to bring out the variegation. Painted Lady has a darker green leaf with no variegation.
4. Chickasaw makes a good basket plant, unlike Painted Lady which has a weaker stem and longer internodes.

DESCRIPTION OF THE PHOTOGRAPH

The accompanying colored photograph illustrates the overall appearance of the cultivar Chickasaw showing the colors as true as reasonably possible for this type of colored reproduction. However, under low light and cool temperatures the flower color darkens; under the low light of winter, the variegation may not show. Under high light the variegation width increases and becomes more distinctive. The photograph illustrates the leaf variability under different environmental conditions.

DETAILED DESCRIPTION

The following detailed description of Chickasaw was based on observations made of the new cultivar on Jan. 13, 1977.

PLANT

Name: Chickasaw
Origin: Seedling 76-22-1 of cross pollination of unpatented pistil parent 75-8 and unpatented pollen parent 75-14.
Form: Upright with spreading tendency.
Height to flowering: 15 to 30 cm.
Growth: Moderate.
Type of cutting: Terminal or stem.
Rooting time: Typical, 10–14 days.
Rooting habit: Fast, dendritic.

FOLIAGE

Arrangement: Lower leaves opposite (usually just one set); upper foliage of any break whorls of 3 with a few 4's.
Shape: Older leaf in oblanceolate, newer leaves are elliptic.
Tip: Obtuse to abruptly acuminate.
Base: Attenuate.
Margin: At base ciliate to finely serrulate at tip.
Venation: Pinnate.
Size: Blade and petiole 8.5 to 9 cm., length of blade 7 to 8 cm., width at widest point 3 to 3.5 cm.
Surface:
*Smoothness.*—Occasionally crinkled.
*Texture.*—Glabrous, typically waxy.
Variegation: Light and high fertilization influence both size of the leaf and variegation observed. High light and age of cutting increase variegation, whereas low light and high fertilization reduce variegation and increase leaf size.
Color:
*Petiole.*—52B.
*Veins.*—48C, upper veins fade.
*Leaf.*—a. Upper 137A. b. Lower 138B.
*Variegation.*—a. Edge 154A. b. Middle 10C. c. Center 10C.

STEM

Color: 50B (variable, nodes darker).
Internode:
*Length.*—Moderate.
*Size.*—Small to moderate.
Node expanded (relative to internode): Little, if any.
Breaking action: Very good.

FLOWER

Form: Typical.
Borne: End of branches, terminal.
Blooming habit:
*Relative number.*—Very good to profuse.
*Time to flowering.*—Short, as with Longwood's Painted Lady.
*Longevity.*—Typical, 3-5 days.
Size of mature flower: First flower on a plant may be small.
*Length.*—4.0 to 5 cm.
*Width.*—4.0 to 4.5 cm.
*Spur.*—5.0 to 5.5 cm.
Color: Lighter pink under high light and heat.
*Eye.*—58B.
*Middle.*—52B through D depending on age and portion of petal.
*Edge.*—Whitish trim on outer edge of flower — 36D.
*Pedicel.*—49A.

REPRODUCTIVE ORGANS

Stamen:

| | |
|---|---|
| 1. Anthers<br>2. Filaments | Typical, fused hood over pistil |

*Pollen.*—a. Color: 158C. b. Abundance: Typical, plenty.
Pistils:

| | |
|---|---|
| 1. Style<br>2. Ovaries | Typical but small |

OTHER CHARACTERISTICS

Disease: Chickasaw is no more susceptible than other varieties to most soft rots.

I claim:

1. A new and distinct form of Impatiens plant as described and illustrated known by the cultivar name Chickasaw and particularly characterized by short internodes; many rose-pink flowers in the summer and salmon flowers in the winter; a bright yellow variegation on a moderately light green leaf under high light and increasing age of plants; and a stem and breaking action conducive to making a good basket.

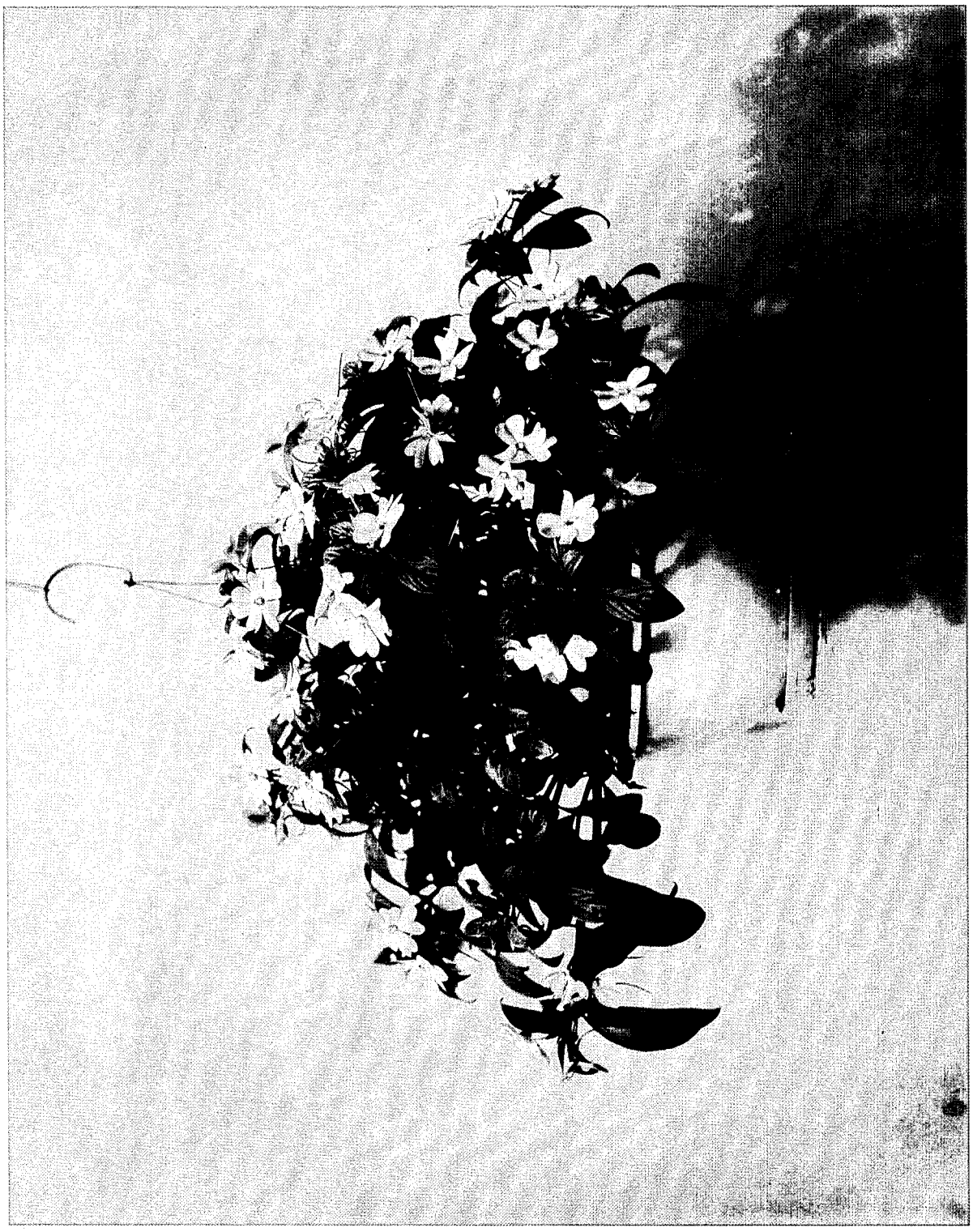

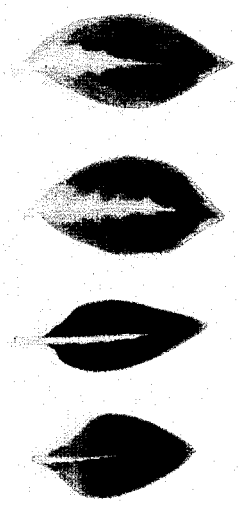

* * * * *